(12) United States Patent
Onishi

(10) Patent No.: US 7,223,976 B2
(45) Date of Patent: May 29, 2007

(54) CHARGED PARTICLE BEAM APPARATUS

(75) Inventor: Takashi Onishi, Mito (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/437,638

(22) Filed: May 22, 2006

(65) Prior Publication Data

US 2006/0289753 A1 Dec. 28, 2006

Related U.S. Application Data

(62) Division of application No. 10/902,255, filed on Jul. 30, 2004, now Pat. No. 7,064,324.

(30) Foreign Application Priority Data

Jul. 30, 2003 (JP) ............................. 2003-203801

(51) Int. Cl.
*G01N 21/88* (2006.01)
(52) U.S. Cl. ................... 250/310; 250/305; 250/505.1; 378/34

(58) Field of Classification Search ................ 250/310, 250/305, 505.1; 378/34
See application file for complete search history.

(56) References Cited

U.S. PATENT DOCUMENTS 6,545,272 B1 4/2003 Kondo
7,064,324 B2 * 6/2006 Onishi ........................ 250/310

FOREIGN PATENT DOCUMENTS

JP 9-245716 9/1997
JP 2002-248338 9/2002

* cited by examiner

*Primary Examiner*—Kiet T. Nguyen
(74) *Attorney, Agent, or Firm*—McDermott Will & Emery LLP

(57) ABSTRACT

The charged particle beams is provided, which can analyze contamination of the inner wall of the system without being disassembled and supply information on appropriate maintenance timing. The contamination level of the inner wall of the system is identified by measuring the spectrum of the X-rays emitted from the inner wall due to irradiation of a charged particle beam or a recoil electron.

1 Claim, 7 Drawing Sheets

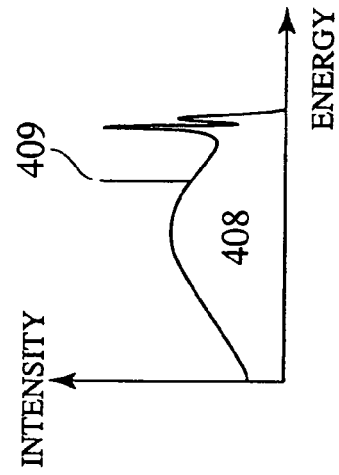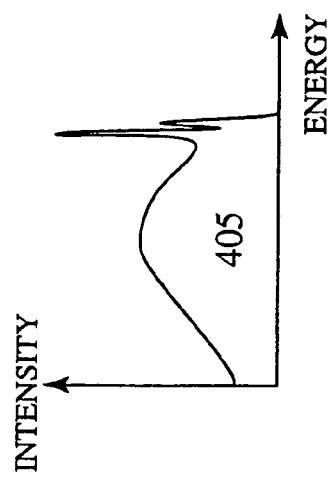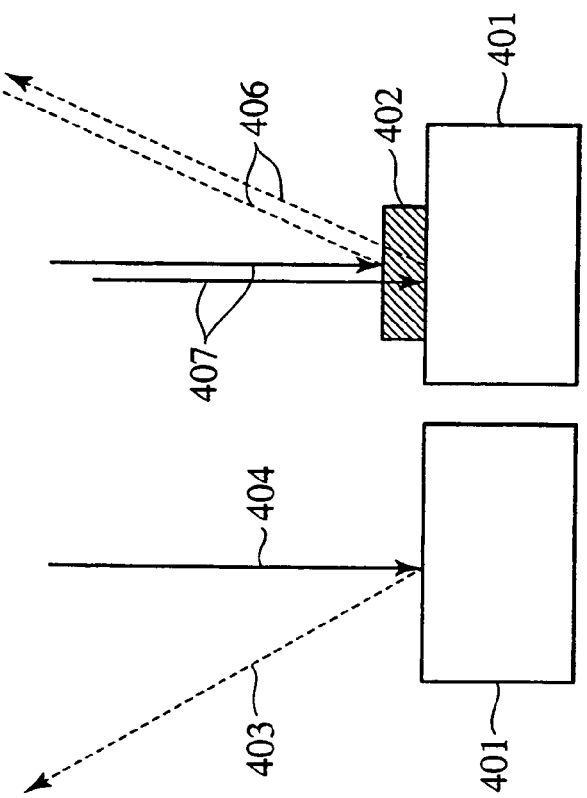

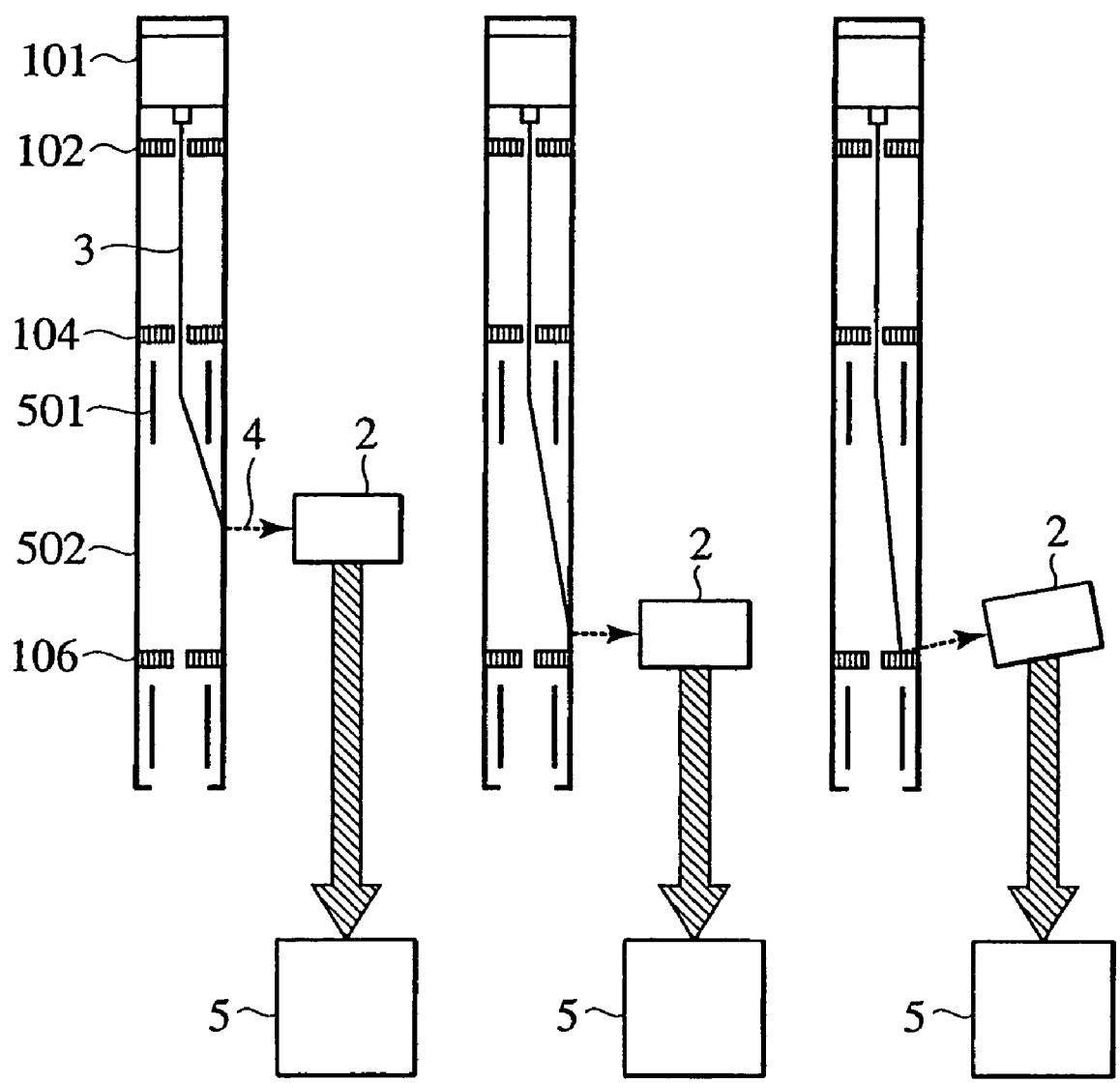

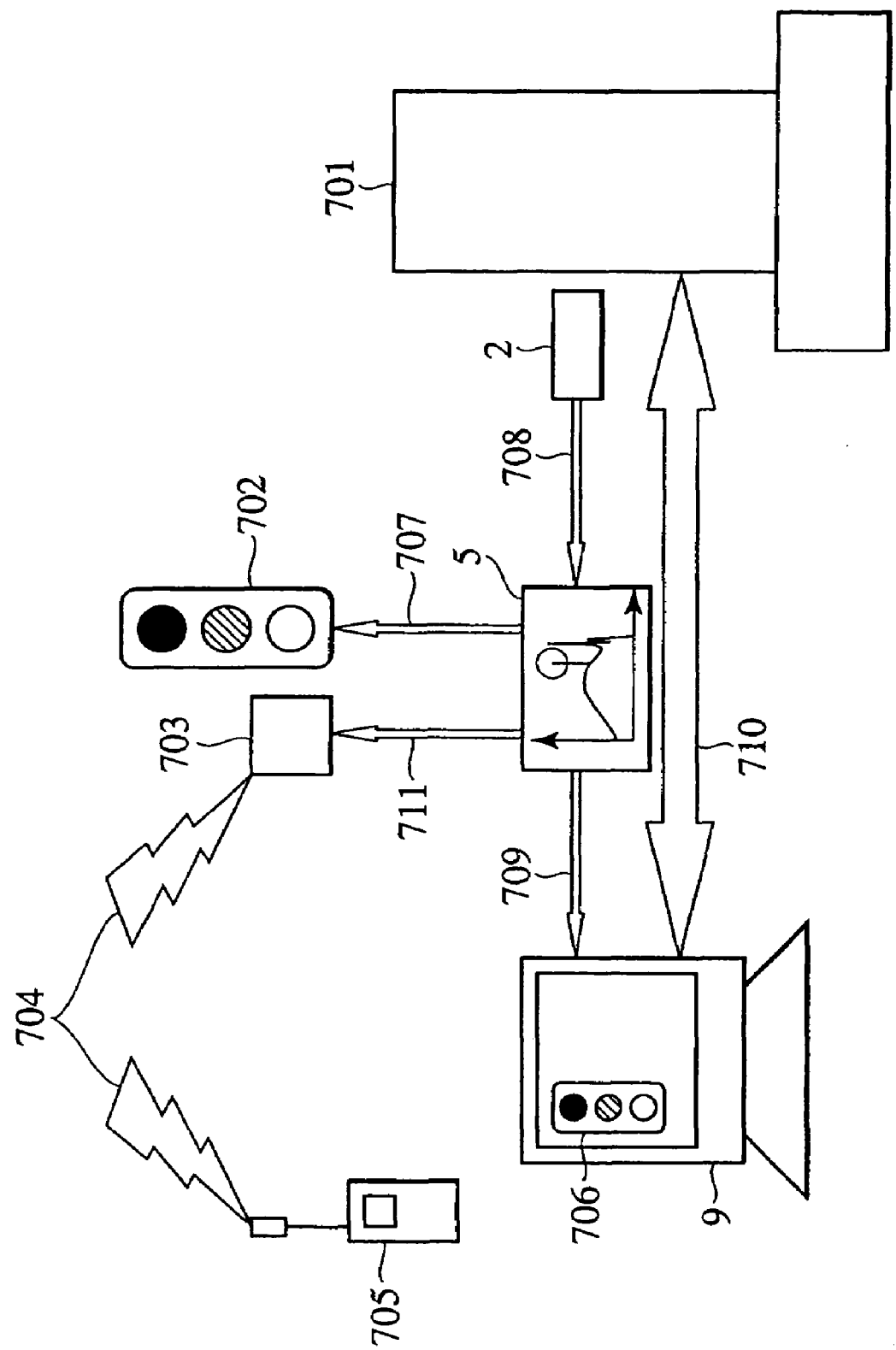

CHARGED PARTICLE BEAM APPARATUS

RELATED APPLICATION

This application is a divisional of application Ser. No. 10/902,255, filed Jul. 30, 2004 now U.S. Pat. No. 7,064,324, which claims priority of Japanese Application No. 2003-203801, filed Jul. 30, 2003, the contents of which are hereby incorporated by reference.

TECHNICAL FIELD

The present subject matter relates to techniques and equipment using charged particle beams, including: an electron beam lithography system that uses electron beams to draw (logic) circuit patterns on semiconductor wafers or the like, an electron microscope that uses electron beams to obtain enlarged images of objects, and other systems that use electron beams or ion beams.

BACKGROUND

There are several problems relating to the systems using charged particle beams, such as an electron microscope and an electron beam lithography system. Each system internally has a beam source for generating a charged particle beam such as an electron beam or ion beam, thin down the charged particle beam into a smaller diameter by using electromagnetic lenses and the like, and irradiate the charged particle beam onto a target. One problem is that there is the necessity for periodic maintenance due to contamination of the inner wall of a beam duct in which the charged particle beam is to travel. Other elements of the system also may need periodic decontamination.

The charged particle beam is irradiated onto a target using electromagnetically formed electron optics or ion beam optics (charged particle optics), and the duct in which the charged particle beam is to travel needs to be maintained in a vacuum to ensure a high mean free pass for the charged particle beam. For this reason, the components of the charged particle optics, such as electromagnetic lenses, permanent magnet lenses, electric/magnetic deflectors, and elements having apertures, are arranged on the periphery of, or partly inside, a vacuum chamber.

Although this vacuum vessel is maintained in a vacuum during the operation of the system using charged particle beams, the performance limits of vacuum pumps make it difficult to completely remove oil-containing or other residual gases or degas the charged particle beam target. Continued operation of the system causes a highly reactive part of molecules (radicals) or the like due to interactions between the residual gases and the charged particles, and thus contaminates the inner wall of the vacuum vessel and other internal structures of the system. The effects of contamination with the hydrocarbon heavily contained in the residual gases are particularly significant, and the hydrocarbon causes the contamination to accumulate on the internal components of the vessel.

The charged particle beam has a charge and is therefore deflected by an electromagnetic field. However, the charged particle beam is significantly affected by internal contamination of the vacuum vessel, in particular. This event is considered to be due primarily to the fact that the formation of insulation films on the surfaces of metallic components due to the contamination produces a residual charge due to a recoil electron or the like and thus causes a local electric field to be formed. To stabilize the course of the charged particle beam and maintain system performance, therefore, it is essential to maintain the cleanliness of the elements having apertures of the system, the elements having apertures periphery, and other sections, by cleaning each of these elements periodically or replacing parts. Such maintenance is particularly important for the system internal structures disposed at the positions near the beam duct where recoil electrons concentrate.

To clean the system interior, however, it is necessary in most cases to stop the vacuum pumps and then introduce the atmosphere into the system before disassembling it, and for this reason, normal operation of the system needs to be stopped. It is desirable that the use of such a procedure be avoidable, since this procedure not only requires great amounts of expenses, but also incites a decrease in productivity due to a decrease in system availability according to the particular shutdown period of the system. A system that allows internal contamination to be removed by introducing a gas without disassembling the system (refer to, e.g., Japanese Patent Laid-open No. 9-245716), and a system that retards contamination by forming a catalyst on an inner wall (refer to, e.g., Japanese Patent Laid-open No. 2002-248338), are known as conventional systems using charged particle beams. However, if the frequency of system cleaning can be reduced by examining the degree of contamination, great contributions can be made to the improvement of productivity.

SUMMARY

Although, above prior art techniques can remove or control the contamination, it can not confirm an extent of contamination or when the cleaning of the internal structure in the charged particle beam apparatus needed without dismantling the charged particle beam apparatus.

An object is to provide: a charged particle beam system that can analyze the contamination of the internal structures or confirm an appropriate maintenance timing without being disassembled.

In order to analyze the contamination of the internal structure without being disassembled, an X-ray emitted from an internal structure of a charged particle beam apparatus with irradiation of charged particle beam, and the detected X-ray is analyzed whether a characteristic X-ray of a contaminant is comprised.

A charged particle beam apparatus comprising: a charged particle gun for emitting a charged particle beam, a converging lens for converging the charged particle beam, a specimen stage for putting a specimen on, a deflector for deflecting the charged particle beam to an inner structure of a vacuum chamber in the charged particle beam apparatus, an X-ray detector for detecting X-ray emitted from an inner structure of the charged particle beam apparatus, and a processor for analyzing the detected X-ray to determined if the detected X-ray comprises a characteristic X-ray of a contaminant.

According to above subject matter, the contamination adhered to the inner structure can be detected by detecting the characteristic X-ray of the contaminant material, as distinct from the inner structure.

Furthermore another object is to provide a charged particle beam apparatus that can confirm an appropriate maintenance timing without being disassembled without dismantling the charged particle beam apparatus. In order to confirm the maintenance timing, an X-ray radiated from an internal structure of a charged particle beam apparatus with irradiation of charged particle beam is detected, and a warning for encouraging cleaning or changing the inner structure of the charged particle beam is issued when a value of a characteristic X-ray regarding to a contamination exceeds a predetermined value.

According to above subject matter, an operator can judge when the cleaning of the inner structure should be done.

The further detailed composition and effects of the present subject matters are made obvious in the following description of exemplary embodiments.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIGS. 4A to 4D are diagrams showing the difference between the X-ray energy spectrum obtained when contamination is present on the metallic wall used in the embodiment of the present invention, and the X-ray energy spectrum obtained when contamination is not present on the metallic wall;

FIGS. 5A to 5C are longitudinal sectional views of a system using charged particle beams, explaining the procedure and method for searching for contamination of the inner wall of the system by using a special-purpose deflector;

FIG. 7 is a schematic diagram showing the configuration of a system which transmits to an operator or the like the characteristic X-ray intensity information obtained in one embodiment.

DETAILED DESCRIPTION

In the following detailed description, numerous specific details are set forth by way of examples in order to provide a thorough understanding of relevant teaching. However, it should be apparent to those skilled in the art that the present teaching may be practiced without such details. In other instances, well known methods, procedures, components, and circuitry have been described at a relatively high-level, without detail, in order to avoid unnecessarily obscuring aspects of the present concepts.

Figure 1:
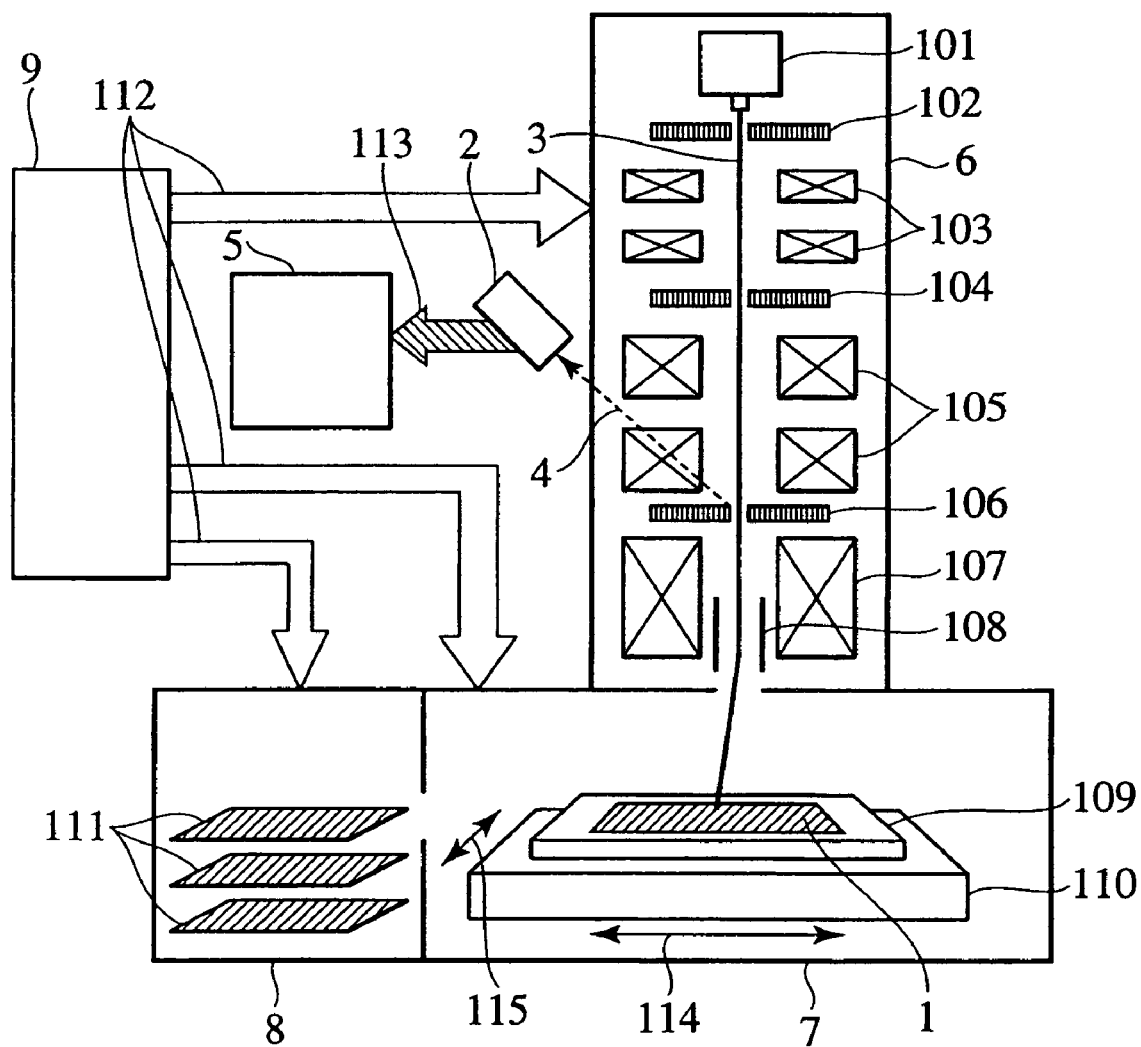
FIG. 1 is a longitudinal sectional view showing schematically an electron beam lithography system.

FIG. 1 is a longitudinal sectional view representing the schematic configuration of an electron beam lithography system as an example of a system or apparatus which uses charged particle beams. In FIG. 1, numeral 6 denotes electron optics having a function which generates and converges electron beams. After being generated by an electron gun 101, an electron beam 3 is first accelerated to an energy of several tens of electron volts, depending on a particular electrical potential difference with respect to an anode 102. Next, the electron beam 3 is shaped and thinned down into a smaller diameter by elements 104, 106 for passing a part of the electron beam 3, and for limiting the other part of the electron beam 3 passing, and electromagnetic lenses 103, 105, 107, then deflected by an electron beam deflector 108, and irradiated onto a target 1 as a specimen to draw circuit patterns or the like thereon.

The target 1 is fixed to a target-holding unit 109 as a specimen stage within a target device 7 including a target chamber, and can be moved in a horizontal direction on a target-moving unit 110. The target is automatically replaceable with another replacement target 111 set in a target changer 8 which includes a target loader, and patterns can be continuously drawn on a plurality of targets. Electron optics 6, the target device 7, the target changer 8, etc. are controlled by a control computer 9 so as to allow unattended operation of the system. As above described, various inner structures compose of the charged particle beam apparatus in vacuum chamber of the charged particle beam apparatus.

The electron beam that has been generated by the electron gun 101 is attracted to the anode 102 having a plus electrical potential. The electron beam is then introduced by the electromagnetic lens 103, the element 104, the electromagnetic lens 105, the element 106, the electromagnetic lens 107, and the electron beam deflector 108, in that order, so as to be irradiated onto the target 1. These elements 104 and 106 have apertures for limiting the charged particle beam passing and are arranged between the electron gun 101 and the target holding unit 109.

The flow of control information from the control computer 9 to the electron beam lithography system is as shown by an arrow 112. The control computer 9 has a processor which controls the charged particle apparatus built-in. The computer performs a sequence of operations according to executable code embodied in a readable medium, when the program is installed in the control computer 9. As described later, the computer analyzes a characteristic X-ray.

Aspects of the methods outlined above may be embodied in software, e.g. in the form of program code executable by the computer or other programmable device 5. Such software typically is carried on or otherwise embodied in a medium or media. Terms such as "readable medium" used herein refer to any medium that participates in providing one or more instructions and/or data to a programmable processor, such as a CPU for execution or other processing.

In this process, an X-ray 4 is emitted from the element 106 due to the irradiation of the electron beam 3. The X-ray 4 is detected by an X-ray detector 2 and then as shown by an arrow 113, sent to an X-ray energy spectrum analyzer 5. The X-ray energy spectrum analyzer 5 converts X-ray analysis signals into an energy distribution and sends the information thus obtained, to the control computer 9.

The X-ray detector 2 and the X-ray energy spectrum analyzer 5 are collectively referred to as an X-ray detection means. For example, the X-ray detector 2 is arranged for detecting the X-ray radiated from the element 106, or arranged on the electron gun 1 side against the element 106.

The target-moving unit 110 moves in directions of arrows 114 and 115, both of which denote the operation of the target-moving unit, and thus changes a position of the target 1 subjected to irradiation.

Next, a technique for analyzing a contamination level from the detected X-ray is described below. FIG. 2 is a schematic diagram of the atoms generated when an electron beam is irradiated onto a target.

Figure 2A:
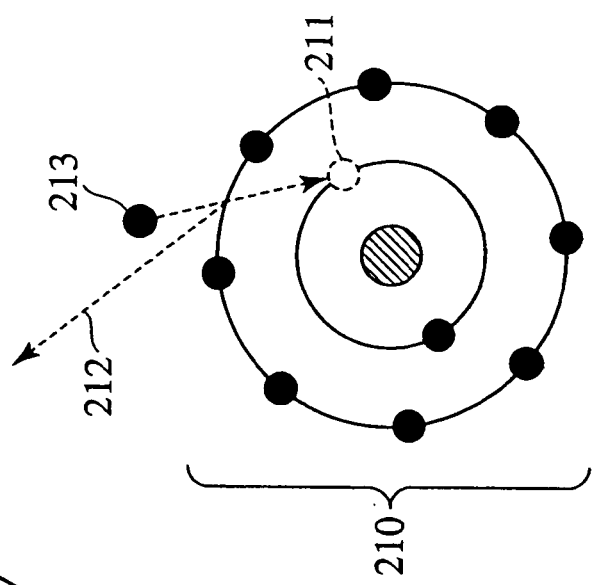
FIGS. 2A to 2C are schematic diagrams explaining how an atom of the substance to which an electron beam has been irradiated emits a characteristic X-ray.

In FIG. 2A, an atom 201 is one of the atoms constituting the target, and electrons 203, 204 are arranged around a nucleus 202. When the constituting elements of the atom 201 are schematically represented in this way, the orbit 205 closest to the nucleus is called the K-shell, and electrons 203 traveling round this orbit are referred to as the K-shell electrons. Likewise, other orbits are named the L-shell, the M-shell, etc. in order of proximity to the nucleus. Orbits down to the L-shell 206 and electrons down to L-shell electrons 204 are shown in the figure.

Figure 2B:
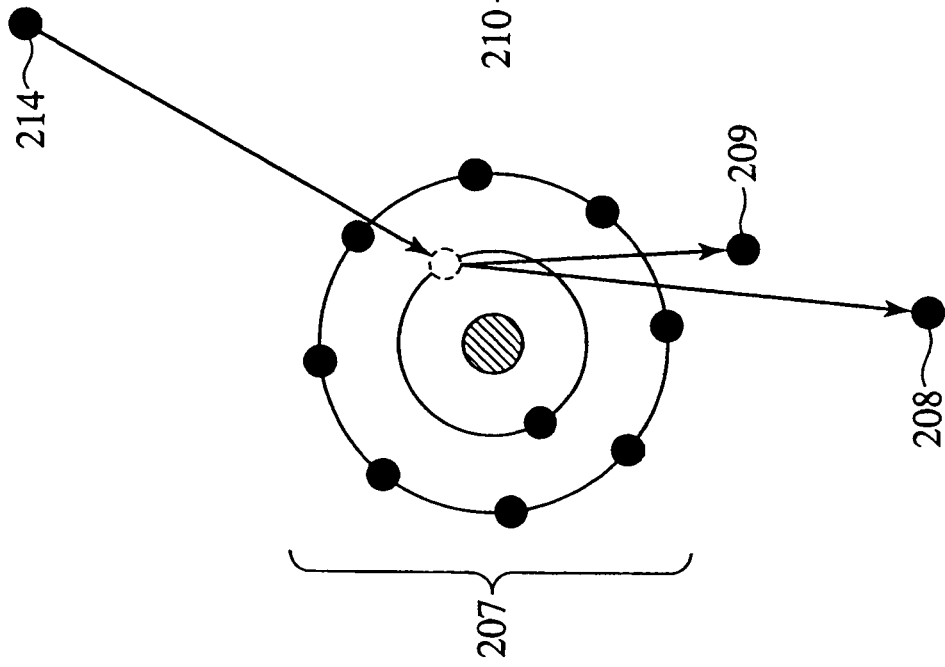
Figure 2C:
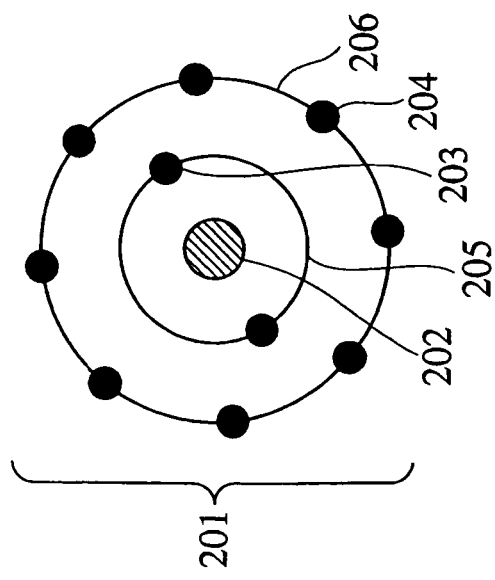

A high-speed (high-energy) electron that is a portion of the electron beam 3 irradiated onto the target 1 enters the atom. As shown in FIG. 2B, in general, in a majority of systems using charged particle beams, including electron beam lithography systems, the irradiated electron 208 has an energy great enough to excite the atom 207, regardless of its kind, and emit an X-ray. Furthermore, for almost all kinds of atoms, except for several kinds of particularly heavy atoms such as a uranium atom, the above energy is great enough to make the K-shell electrons 203 recoil. An atom 207 that has lost one K-shell electron 203 in the form of a secondary electron 209 by means of the incident electron 208 soon captures either of peripheral electrons 213 at the resulting vacancy in a K-shell 211 and emits differential energy in the form of an electromagnetic wave as illustrated in FIG. 2C. An X-ray 212 includes a wavelength indicates a character depending on a kind of materials. Of all X-rays emitted from an atom, only those generated with the K-shell and other inner-shell electrons as its cause, are referred to as the characteristic X-rays of the atom. Numeral 210 denotes an atom that emits characteristic X-rays, numeral 212 the characteristic X-rays emitted, numeral 213 an electron filling the resulting vacancy, and numeral 214 a high-speed (high-energy) electron incident on the atom.

Figure 3:
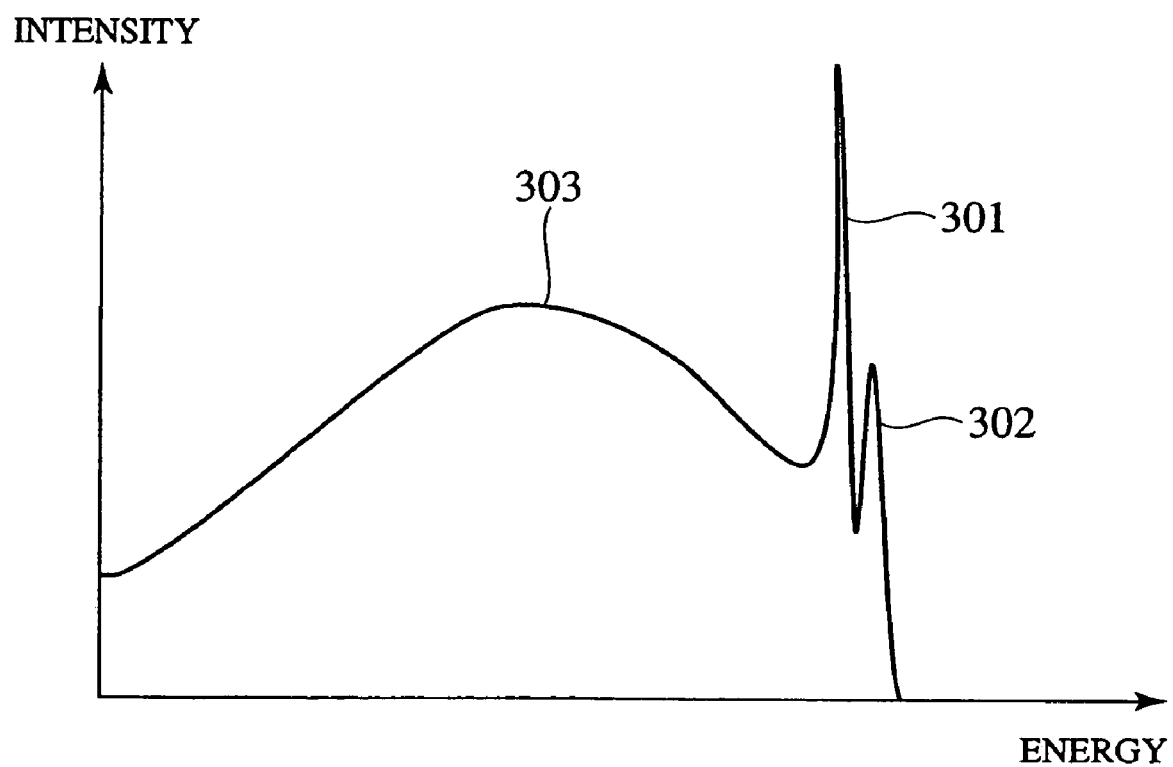
FIG. 3 is a diagram showing the X-ray energy spectrum obtained.

FIG. 3 is a conceptual diagram showing schematically the energy spectrum of the X-rays monitored. The X-ray spectrum obtained by irradiating an electron beam onto a substance is composed of the continuous X-rays 301 having an electron beam bremsstrahlung energy, and characteristic X-rays such as a sharply peaked X-ray 302 and an X-ray 303.

In the above-described beam source for generating characteristic X-rays, the energy or wavelength of the characteristic X-rays is characteristic of the kind of atom, and thus, the kind of atom emitting an X-ray can be identified by measuring the wavelength of the characteristic X-rays.

Therefore, by checking the wavelength obtained of the characteristic X-rays against the atomic numbers of the atoms which constitute carbon and hydrogen or the inner wall (the inner wall forming the beam duct for the charged particle beam), it is possible to examine whether contamination is present and with approximately what density it is present. The accumulation level of the contamination can thus be identified without shutting down the electron beam lithography system.

For example, in case of the different atoms from materials consisting of the inner structure in the vacuum chamber different X-ray spectra are detected, and there is a possibility that the contamination adheres to the inner structure. Therefore it is possible to check an existence of contamination being not same element as the inner structure.

The identification of contamination is described below. In FIGS. 4A and 4C, an electron 404 and electrons 407, respectively, are irradiated onto a metallic wall surface 401. If the wall surface 401 is dirty with contamination 402 as shown in FIG. 4C, when the energy spectra of the X-ray 403 and X-rays 406 emitted are analyzed, an energy spectrum 405 of the X-ray emitted from a non-contaminated wall surface and an energy spectrum 408 of the X-rays emitted from the contaminated wall surface assume different aspects. These states are shown in FIGS. 4B and 4D, respectively, and the difference between the two types of spectra is due to the fact that the constituting atoms differ in atomic number between the irradiated substances. More specifically, the peak energy of the characteristic X-rays of contaminant 402 appears as a new peak 409 at a position different from the peak of the spectrum 405 produced by the wall 401 alone. Since the energy of the peak 409 is univocally determined by the atomic numbers of the substance, the atomic numbers of the contamination and its quantity can be identified from the position and height of the peak 409.

An object in this case is to identify the appropriate maintenance timing for the elements, the deflector, and the parts constituting the inner wall of the beam duct, and perform the appropriate maintenance. To link identification information on maintenance timing and information on the contamination detected by means of X-rays, it is useful to obtain information for judging at what level of what peak of the spectrum any necessary part replacements are to be performed, and information for judging what parts at what positions of the system are to undergo the maintenance.

The former of the above two judgments can be based on the system performance analyzed using other measuring means. For an electron beam lithography system, for example, an experimental system is first operated until the local position accuracy of the electron beam has decreased, then the X-ray spectrum under this state is acquired, and a reference ratio between the peak height of the contamination and the peak height depending on the type of metal is created. For a system that is to be operated as an practical product, both sets of information mentioned above can be used to replace parts before the local position accuracy decreases, and also to make a distinction between performance deterioration due to contamination and performance deterioration caused by other factors. For example, a predetermined value was determined in advance, and then upon detecting the peak height exceeding the predetermined value, it is possible to warn for encouraging cleaning or changing the inner structure of the charged particle beam. The warning lets an operator know the maintenance timing with a display or sound.

The latter judgment is described next. The criteria for judging what parts are to undergo maintenance can likewise be derived using an experimental system. At the same time, however, what positions on the inner wall of the system are significantly contaminated can also be detected by using a special-purpose charged particle deflector provided in the system or by diverting to that purpose a charged particle deflector equipped for other purposes.

Examples of using a special-purpose deflector are shown in FIG. 5. The systems using charged particle beams, shown in FIGS. 5A, 5B and 5C, are identical ones.

The beam passage for the charged particle beam is formed with an inner wall 502 along an optical axis of the charged particle beam, in which are arranged an electron gun 101 (charged particle source), a element 106, an electron beam deflector 108, and a special-purpose electron beam deflector 501. An electron beam (charged particle beam) 3 that has been emitted from the electron gun 101 is irradiated onto a target through the beam duct. In the beam duct, the electron gun 101, the element 106, and the electron beam deflector 108 can also be arranged so that part thereof faces in parallel to a traveling direction of the electron beam. The beam duct is maintained in a high degree of vacuum to ensure that the charged particle beam properly reaches the target without attenuating.

The charged particle beam 3 is deflected using the special-purpose electron beam deflector 501, and then irradiated onto the inner wall 502 or the element 106. By monitoring with a detector 2 the X-ray 4 emitted from the inner wall 502 or the element 106, it is possible to identify whether the irradiated section is contaminated and at what position the contamination (if detected) is significant, and therefore to judge whether the component of that section is to undergo maintenance. Information that has thus been obtained becomes even more effective when used in conjunction with the information that represents the relationship between contamination and performance.

As described above, the contamination of components at any position inside the system can be detected using a special-purpose deflector or a deflector sharable with other elements. However, even when no such deflector is used and the system is in an operating state, approximate information on contamination can likewise be obtained by using an X-ray detector placed at an appropriate position in the system.

This detection means is described below using FIG. 6.

Figure 6:
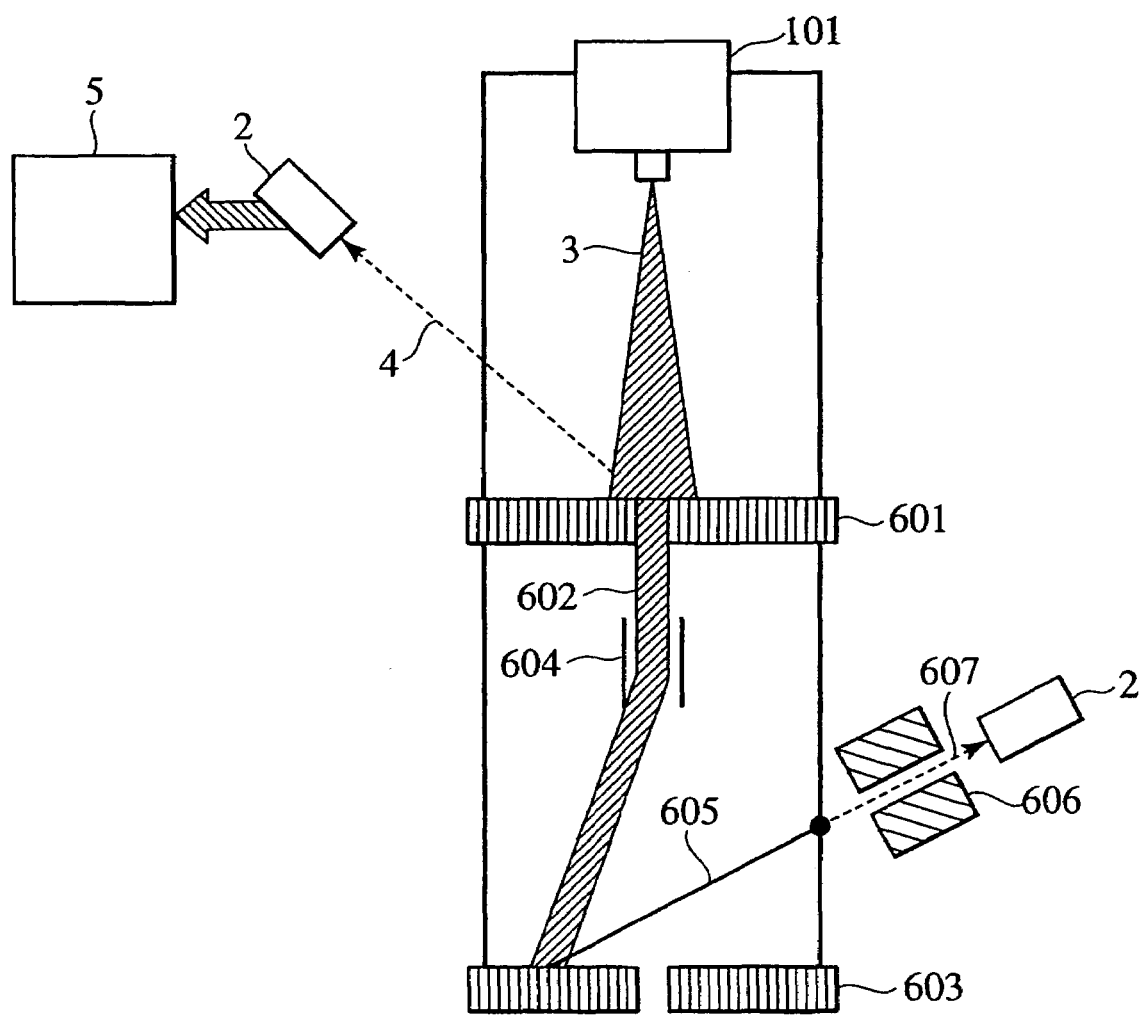
FIG. 6 is a diagram showing the unit for detecting the X-ray generated by irradiation of a charged particle beam to an internal structure of the system used, and the X-ray generated by the electron produced by the above irradiation.

FIG. 6 shows an electron beam lithography system when it is in operation, and this figure, unlike FIG. 1, represents an electron beam 3 realistically so that it has a spatial spread. In general, in a system using charged particle beams, a generated electron beam is collimated in several split phases by use of elements having an aperture for passage of the beam and the remaining particles of the electron beam are irradiated onto a target. This also applies to FIG. 6, in which the electron beam 3 is collimated into an electron beam 602 by an element 601.

In addition, a unit called the "blanker" is equipped to turn beam irradiation onto the target on and off at high speed, and electron beam components not irradiated onto the target are deflected and irradiated to a specific collimating section inside the system and stopped there. In FIG. 6, how the electron beam is stopped by a blanker 604 via an element 603 is schematically represented. By using an X-ray detector to analyze the X-rays emitted from the system during operation, these electron beam irradiation sections such as the elements having an aperture for passage of the beam can be checked for contamination.

The internal components of the system that undergo irradiation of an electron beam during the operation of the system usually become hot and are located near a passageway of the electron beam. Therefore, these components are highly prone to, and most significantly affected by, contamination, and are thus appropriate as the sections to be subjected to contamination monitoring based on characteristic X-ray analyses.

In addition, it is more or less meaningful to perform characteristic X-ray analyses on sections other than the elements having an aperture for passage of the beam, i.e., sections not directly undergoing irradiation of the electron beam during the operation of the system. In FIG. 6, the elements having an aperture for passage of the beam that have undergone the irradiation of the charged particle beam reflect electrons, called "recoil electrons", to the periphery. These electrons are generated by the scattering of the electrons contained in the atoms of the beam-irradiated substance, or by, when the irradiated charged particle beam is an electron beam, the reflection of an incident electron by an atom present inside the irradiated substance. There are not few cases in which these secondary electrons each have energy large enough to generate an X-ray in the internal structure of the system, around the elements having an aperture for passage of the beam. This X-ray can also be used to perform contamination checks on the system internal structure around the elements having an aperture for passage of the beam. FIG. 6 shows how a recoil electron 605 is generated by the irradiation of the electron beam 602 onto the element 603 and collides with the inner wall of the beam duct in order for an X-ray 607 to be emitted. In an actual system, the intensity of the X-ray emitted from the element having an aperture for passage of the beam itself is very high, in other words, the secondary electrons are smaller than the primary charged particle beam in terms of energy and quantity. Therefore, care is required so that the X-ray emitted from a specific section, not the X-ray emitted from the element 603, will be detected using an X-ray collimator 606 or the like.

The use of the contamination information mentioned above makes it possible to realize a system that constantly monitors itself and notifies an operator of its own states. This system is described below in line with a block diagram of FIG. 7.

For a system 701 that uses charged particle beams, in which an X-ray detector 2 is equipped as a contamination-monitoring unit, data on the peaks of characteristic X-rays associated with a specific type of contamination is constantly acquired and energy-spectral distribution curves are created at fixed time intervals using a detector 2. If a fixed amount of energy is exceeded on these curves, indication information 706 indicating that maintenance is required (i.e., maintenance information displayed on a display unit of a control computer 9) will be transmitted to the operator through a special-purpose signal machine 702 (for specifying maintenance timing to the operator) or the control computer 9.

An arrow 707 schematically represents the flow of information from an X-ray energy spectrum analyzer 5 to the system component which specifies maintenance timing to the operator. An arrow 708 schematically represents the flow of information from the X-ray detector to the X-ray energy spectrum analyzer 5. An arrow 709 schematically represents the flow of information from the X-ray energy spectrum analyzer to the control computer 9. An arrow 710 schematically represents in collective form the flow of control information between the control computer and the system which uses charged particle beams, and the flow of various information on the current state of the system. An arrow 711 schematically represents the flow of information from the X-ray energy spectrum analyzer to an information device which transmits maintenance timing information.

For the detector, part of its function set can also be included in the control computer 9. In addition, information can be sent directly to a serviceman or the like through, as another information transmission route, an information device 703 transmitting maintenance timing information and information transmitting paths 704, such as the Internet or wireless (i.e., a thunderbolt-shaped image 704 schematically representing the Internet, wireless or other information routes). The serviceman has a hand-held type of receiving device 705 for the maintenance timing information possessed by a person at a location remote from a special device for a serviceman or the like.

Contamination checking with a special-purpose or other-purpose charged particle deflector can be periodically executed as a "contamination checking process", whereby it also becomes possible to realize a system capable of obtaining further detailed contamination information.

As set forth above, according to the present embodiment, in an electron beam lithography system, it is possible to monitor the accumulation level of contamination on the inner wall of the system without disassembling it and identify appropriate maintenance timing, and thus facilitating the maintenance. Since the maintenance can be performed in appropriate timing, it is possible to provide an electron beam lithography system operating with high efficiency or a highly efficient lithography method.

According to the present invention, by analyzing characteristic X-rays, the contamination of the inner wall of a system which uses charged particle beams can be detected without disassembling the system, and thus, maintenance of the system can be easily performed.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A program product for deciding a maintenance timing of a charged particle beam apparatus comprising a charged particle gun for emitting a charged particle beam, a converging lens for converging the charged particle beam, a specimen stage for putting a specimen on, and an X-ray detector for detecting X-ray radiated from an inner structure of the charged particle beam apparatus, the product comprising: executable code embodied in a readable medium, execution code causing the apparatus to perform a sequence of steps comprising:

detecting an X-ray emitted from the inner structure;

detecting an X-ray of a contaminant included in the detected X-ray; and judging whether the value of characteristic X-ray exceeds a predetermined value or not to determine whether or not maintenance is appropriate.

* * * * *